United States Patent

Tanaka et al.

[11] Patent Number: 5,972,635
[45] Date of Patent: Oct. 26, 1999

[54] SULFONIC ACID GROUP BUFFERED DRY ANALYTICAL ELEMENT FOR QUANTITATIVE ANALYSIS OF CREATINE KINASE OR ITS MB ISOZYME

[75] Inventors: Hideaki Tanaka; Yoshihiko Abe; Yoshiki Sakaino; Kaoru Terashima, all of Saitama, Japan

[73] Assignee: Fuji Photo Film Co., Ltd., Kanagawa, Japan

[21] Appl. No.: 09/158,485

[22] Filed: Sep. 22, 1998

[51] Int. Cl.$^6$ .................................................. C12Q 1/50
[52] U.S. Cl. ................ 435/17; 435/7.4; 435/188
[58] Field of Search .................. 435/17, 7.1, 7.4, 435/188, 194, 805; 422/55–60

[56] References Cited

U.S. PATENT DOCUMENTS

| | | |
|---|---|---|
| 4,067,775 | 1/1978 | Wurzburg et al. . |
| 4,080,265 | 3/1978 | Antonik .......................... 195/103.5 R |
| 4,387,160 | 6/1983 | Gomez et al. ............................. 435/7 |
| 4,912,033 | 3/1990 | Ladenson et al. ........................ 435/7 |
| 5,298,406 | 3/1994 | Loyd et al. ............................... 435/17 |
| 5,804,394 | 9/1998 | Suzuki et al. ............................ 435/7.4 |

FOREIGN PATENT DOCUMENTS

| | | |
|---|---|---|
| 0200541 | 1/1978 | European Pat. Off. . |
| 0178113 | 4/1986 | European Pat. Off. . |
| 0200540 | 11/1986 | European Pat. Off. . |
| 0426100 | 5/1991 | European Pat. Off. . |
| 0685561 | 12/1995 | European Pat. Off. . |
| WO 95/17520 | 6/1995 | WIPO . |

OTHER PUBLICATIONS

Landt Y. Semi–automated Direct Colorimetric Measurement of Creatine Kinase Isoenzyme MB Activity After Extraction From Serum by Use of a CK–MB Specific Monoclonal Antibody, Clin Chem 34/3 575–581, 1988.

*Primary Examiner*—Ralph Gitomer
*Attorney, Agent, or Firm*—McAulay Nissen Goldberg Kiel & Hand, LLP

[57] ABSTRACT

A dry analytical element for quantitatively analyzing creatine kinase is composed of a support and a creatine kinase-detecting agent layer. The creatine kinase-detecting agent layer contains creatine phosphate and adenosine diphosphate which react with each other to give adenosine triphosphate in the presence of creatine kinase, a buffer compound having a sulfonic acid group which keeps the layer in the range of pH 5.5 to pH 8.5 for the formation of adenosine triphosphate, and an indicator composition which reacts with the formed adenosine triphosphate to give a spectroscopically detectable compound. An analytical element for analysis of creatine kinase MB isozyme further contains in the layer an antibody which specifically inhibits activity of M sub-unit of creatine kinase.

12 Claims, No Drawings

SULFONIC ACID GROUP BUFFERED DRY ANALYTICAL ELEMENT FOR QUANTITATIVE ANALYSIS OF CREATINE KINASE OR ITS MB ISOZYME

FIELD OF THE INVENTION

This invention relates a dry analytical element for quantitatively analyzing creatine kinase or creatine kinase MB isozyme.

BACKGROUND OF THE INVENTION

It is generally known that quantitative analysis of creatine kinase (CK or CPK) in blood sampled from a patient is diagnostic of creeping palsy, dermatomyositis and cardiac infarction. In creatine kinase (CK), there are three isozymes, namely, creatine kinase MM (CKMM), creatine kinase MB (CKMB) and creatine kinase BB (CKBB). These isozymes are mainly present in skeletal muscle (CKMM), cardiac muscle (CKMB), or brain and spinal cord (CKBB), respectively. When cardiac infarction occurs, CKMB in cardiac muscle comes out into blood and accordingly its content in blood increases. Therefore, it is of value for diagnosis of cardiac infarction to assay CKMB in blood.

Methods for assaying creatine kinase and/or creatine kinase MB isozyme had been studied, and a precise assaying method was established.

The method for assaying creatine kinase generally comprises the steps of preparing serum or plasma of the blood sampled from a patient, forming spectroscopically detectable species according to the enzyme activity of creatine kinase contained in the serum or plasma, and measuring the amount of the formed species to determine the content of creatine kinase.

For performing the above analytical method, the following two reaction systems are employable.

1) Reaction System 1

Creatine phosphate (CP) and adenosine diphosphate (ADP) are caused to react in the presence of creatine kinase (CK) contained in the sample (serum or plasma) to form adenosine triphosphate (ATP), while pH condition of the enzyme reaction is adjusted with a buffer working in the pH range of 5.5 to 8.5. The amount of the formed adenosine triphosphate (ATP) is proportional to that of creatine kinase (CK). The thus formed ATP is caused to react with glucose (Glu) in the presence of hexokinase (HK) to prepare glucose-6-phosphate (G6P), and then the prepared G6P is caused to react with nicotinamide adenine dinucleotide (phosphate) in an oxidized form (NAD(P)) in the presence of glucose-6-phosphate dehydrogenase (G6PDH) to produce nicotinamide adenine dinucleotide(phosphate) in a reduced form (NAD(P)H). The amount of the produced NAD(P)H is measured by a spectroscopic method and determined in accordance with the calibration curve beforehand obtained. The content of creatine kinase (CK) is determined from thus determined amount of NAD(P)H.

In order to improve accuracy of the spectroscopic measurement, NAD(P)H can be further caused to react with a tetrazolium salt to form a formazan dye and then the amount of the formazan dye is measured to determine the content of creatine kinase (CK) in the sample (Japanese Patent Provisional Publication No. 63(1988)-32499).

The reaction system 1 described above is represented by the following formulas.

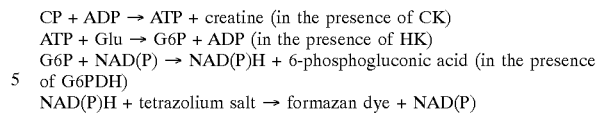

2) Reaction System 2

Creatine phosphate (CP) and adenosine diphosphate (ADP) are caused to react in the presence of creatine kinase (CK) contained in the sample to form adenosine triphosphate (ATP), while pH condition of the enzyme reaction is adjusted with a buffer working in the pH range of 5.5 to 8.5. The amount of the formed adenosine triphosphate (ATP) is proportional to that of creatine kinase (CK). The thus formed ATP is caused to react with glycerol in the presence of glycerol kinase to prepare L-$\alpha$-glycerophosphate, and then the prepared L-$\alpha$-glycerophosphate is caused to react with oxygen in the presence of L-$\alpha$-glycerophosphate oxidase to produce hydrogen peroxide. Finally, thus produced hydrogen peroxide is caused to react with a leuco dye to form a blue dye, and then the amount of the blue dye is measured by a spectroscopic method and determined in accordance with the calibration curve beforehand obtained. The content of creatine kinase (CK) is determined from thus determined amount of the blue dye.

The reaction system 2 described above is represented by the following formulas.

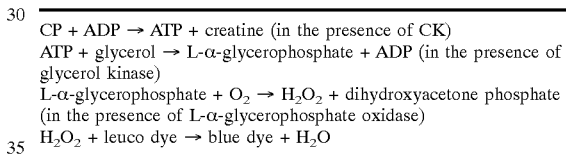

Since creatine kinase has the three isozymes described above, it is not easy to assay creatine kinase MB isozyme. Prior to assaying process, MB isozyme must be isolated from MM and BB isozymes in principle. Practically, the amount of BB isozyme in blood is negligible because it is essentially present in brain and spinal cord, but it is still very difficult to separate MB isozyme from MM isozyme.

For the purpose of obviating the above trouble, Japanese Patent Publication No. 56(1981)-19239 proposes an assaying method in which a particular antibody is employed, instead of isolating MM isozyme from the sample, to inhibit the activity of MM isozyme without adversely affecting that of MB isozyme. The antibody completely inhibits the enzyme activity of sub-unit M in MM and MB isozymes, but on the other hand it does not inhibit the activity of subunit B in MB isozyme. In the method, the sample (serum or plasma) is treated with the antibody (the M sub-unit inactivation antibody) so that creatine kinase in the sample may have only the activity originating from MB isozyme. Thereafter, thus restricted activity is measured by the above reaction system 1 or 2 to assay creatine kinase MB isozyme.

In the conventional assaying process for creatine kinase or creatine kinase MB isozyme, the reactions described above are generally performed in a solution (the process in which the reactions are performed in a solution is referred to as "wet process"). The wet process generally requires relatively long time, and accordingly it takes relatively long time to make a diagnosis based on the wet assaying process. However, for example in the case of cardiac infarction, it is needed to diagnose the case, as soon as possible, because the success of treatment depends on how soon the treatment begins. From this viewpoint, it is preferred to shorten the time to perform the assaying process.

For assaying process which can be performed in relatively short time, a dry analytical element is known. The analytical element generally comprises a transparent support and an agent layer provided thereon which contains a reagent composition participating in the reaction system for detection. For assaying the creatine kinase or creatine kinase MB isozyme, a dry analytical element is also developed and practically used. In the analytical element, the agent layer comprises the reagent composition for the above described reaction system 1 or 2. The detailed description about the dry analytical element for creatine kinase or creatine kinase MB isozyme is given in the following publications; Japanese Patent Provisional Publications No. 61(1986)-254198, No. 61(1986)-254199, No. 61(1986)-260164, and No. 63(1988)-32499.

Although the dry analytical element shortens the time to perform the assaying process, the reagent composition of the analytical element is liable to deteriorate during storage. If the analytical element is stored under ambient conditions, its sensitivity rapidly lowers. For obviating the deterioration of the reagent composition, the known dry analytical element must be stored in a refrigerator. However, it is very inconvenient to need a refrigerator for storing the analytical element, and further such inconvenience for storage often delays beginning of the assaying process and accordingly it often prevents an early definitive diagnosis.

Therefore, it is an object of the present invention to improve the storage stability of dry analytical element for quantitative analysis of creatine kinase or creatine kinase MB isozyme. Particularly, it is an object of the invention to provide a creatine kinase or creatine kinase MB isozyme dry analytical element which does not deteriorate even if stored under ambient conditions and hence which can be stored under ambient conditions, with no need of employing a refrigerator.

SUMMARY OF THE INVENTION

The present invention resides in a dry analytical element for quantitatively analyzing creatine kinase comprising a support and a creatine kinase-detecting agent layer provided thereon, in which said layer contains creatine phosphate and adenosine diphosphate which react with each other to form adenosine triphosphate in the presence of creatine kinase, a buffer compound which has a sulfonic acid group and keeps the layer under pH condition in the range of pH 5.5 to pH 8.5 for the formation of adenosine triphosphate, and an indicator composition which reacts with the formed adenosine triphosphate to give a spectroscopically detectable compound.

The present invention also resides in a dry analytical element for quantitatively analyzing creatine kinase MB isozyme comprising a support and a creatine kinase MB isozyme-detecting agent layer provided thereon, in which said layer contains an antibody which specifically inhibits the activity of M sub-unit of creatine kinase, creatine phosphate and adenosine diphosphate which react with each other to form adenosine triphosphate in the presence of creatine kinase MB isozyme, a buffer compound which has a sulfonic acid group and keeps the layer under pH condition in the range of pH 5.5 to pH 8.5 for the formation of adenosine triphosphate, and an indicator composition which reacts with the formed adenosine triphosphate to give a spectroscopically detectable compound.

The creatine kinase or creatine kinase MB isozyme dry analytical element of the invention is characterized by utilizing a buffer compound having a sulfonic acid group, instead of utilizing a conventional buffer such as Tris and imidazole, as a buffer which gives pH condition suitable for the formation of adenosine triphosphate (ATP) derived from creatine phosphate (CP) and adenosine diphosphate (ADP) with cooperation of enzyme action of creatine kinase or creatine kinase MB isozyme.

DETAILED DESCRIPTION OF THE INVENTION

The aforementioned reaction systems 1 and 2 are employable for the dry analytical element of the invention. Therefore, any indicator composition employed in the aforementioned systems can be employed for the analysis utilizing the analytical element of the invention as the indicator composition which reacts with the formed adenosine triphosphate to give a spectroscopically detectable compound. Examples of the indicator composition are as follows:

1) a composition comprising glucose, hexokinase, nicotinamide-adenine dinucleotide in an oxidized form (or nicotinamide-adenine dinucleotide phosphate in an oxidized form) and glucose-6-phosphate dehydrogenase;

2) a composition comprising glucose, hexokinase, nicotinamide-adenine dinucleotide in an oxidized form (or nicotinamide-adenine dinucleotide phosphate in an oxidized form), glucose-6-phosphate dehydrogenase and a tetrazolium salt; and 3) a composition comprising glycerol, glycerol kinase, L-α-glycerophosphate oxidase and a leuco dye.

In the case that the analyte is creatine kinase MB isozyme, glucose in the above composition 1 or 2 can be omitted because the analyte (i.e., creatine kinase MB isozyme) is contained in blood in a relatively small amount (even if cardiac infarction occurs) and blood naturally contains glucose enough to indicate such a small amount of the analyte.

The dry analytical element of the invention may consist of known components except the above-mentioned particular buffer compound. The examples and detailed explanation about the components other than the buffer compound are described in the above publications, and hence they are omitted in this specification.

With respect to "buffer compound having a sulfonic acid group" of the invention, a detailed description is given below.

Creatine phosphate (CP) and adenosine diphosphate (ADP) react with each other to form adenosine triphosphate (ATP) with the cooperation of enzyme action of creatine kinase or creatine kinase MB isozyme. It is known that the reaction should be performed in the pH range of 5.5 to 8.5. Therefore, Bis-Tris (one of Good's buffers) has been used before so as to ensure the pH condition, but at present a imidazole compound is generally employed in accordance with JSCC recommendation on creatine kinase assay.

The inventors have studied about the aforementioned deterioration of the dry analytical element, and found that the components in the analytical element gradually react with each other even in the absence of creatine kinase (CK) or creatine kinase MB isozyme (CKMB) to cause the deterioration during storage under ambient conditions. In the reaction system 1, the inventors confirmed that CP and ADP partially react with each other to form ATP even in the absence of CK or CKMB and that CP and Glu react with each other to form G6P. It has also been confirmed in the reaction system 2 that CP and ADP partially react with each other to form ATP even in the absence of CK or CKMB and that CP and glycerol react with each other to form L-α-glycerophosphate. These reactions occurring in the absence of CK or CKMB utterly lower accuracy of the assay.

For the purpose of inhibiting the aforementioned troublesome reactions, the inventors have further studied and finally found that a buffer compound having a sulfonic acid group (which can be in the form of sulfonate) can effectively inhibit the troublesome reactions. On the basis of this finding, the inventors have achieved the present invention, that is, the dry analytical element employing the buffer compound having a sulfonic acid group instead of a conventional buffer compound or composition.

The buffer compound having a sulfonic acid group employed for the invention preferably is one of Good's buffers. There are many compounds belonging to Good's buffers. Some of them contain a sulfonic acid group, and the others do not. For the present invention, the former are employed. A detailed description about Good's buffer is given in many known books or publications. Concrete examples of the buffer preferably employed for the invention include Good's buffers of TES, TAPSO, MOPSO, MES, DIPSO, HEPES and HEPSO. Preferred are TES, TAPSO, MOPSO and MES, and particularly preferred are TES and TAPSO. The formulas of TES, TAPSO, MOPSO and MES are given below.

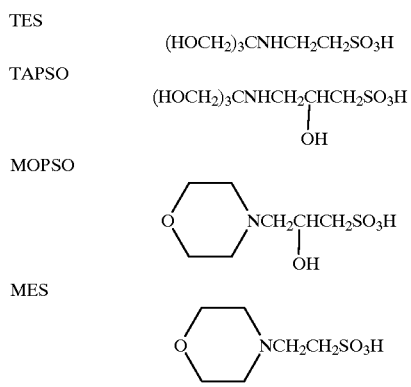

TES
$(HOCH_2)_3CNHCH_2CH_2SO_3H$

TAPSO
$(HOCH_2)_3CNHCH_2CHCH_2SO_3H$
$\qquad\qquad\qquad\quad |$
$\qquad\qquad\qquad\ OH$

MOPSO

MES

The amount of the buffer compound is not particularly restricted, and can be easily determined by preliminary experiments beforehand performed in various amounts of the buffer compound in accordance with general usage of Good's buffer. The buffer compound having a sulfonic acid group can be employed singly or in combination with two or more, and further it can be also employed in combination with other buffer compound or composition having no sulfonic acid group.

The assaying process for quantitatively analyzing creatine kinase or creatine kinase MB isozyme employing the dry analytical element is described in the before-mentioned publications, and the assaying process using the analytical element of the invention can be also carried out in the same manner as is described there.

The present invention is further described by the following examples and comparison examples. In each of the following examples and comparison examples, the dry analytical element employs the reaction system 1 to assay creatine kinase MB isozyme. However, the performance of the buffer compound of the invention is essentially independent of the reaction system (whether it is the reaction system 1 or 2) or the analyte (whether it is total creatine kinase or creatine kinase MB isozyme), and therefore the results of the following examples and comparison examples should be presumed to be the same in any embodiment of the invention.

EXAMPLE 1

Preparation of Analytical Element for CKMB Employing TES as Buffer Compound

A transparent film of polyethylene terephthalate (thickness: 180 μm) was subjected to hydrophilic surface treatment, and then the coating solution consisting of the following components was applied onto the above-treated surface of the film. The applied solution was then dried to form a detecting agent layer having a thickness of 12 μm (in terms of thickness after dryness). The components of the coating solution for detecting agent layer are as follows:

| | |
|---|---|
| Deionized gelatin | 200 g |
| Water | 1,100 g |
| Aqueous 5% solution of nonionic surface active agent | 80 g |
| Nitrotetrazolium blue | 10 g. |

The formed detecting agent layer was wetted with a solution containing a gelatin-crosslinking agent (approx. 30 g/m²), and then a sheet of tricot woven with polyethylene terephthalate yarn was compressed and fixed on the detecting agent layer. Subsequently, the sheet was dried to form a developing layer base.

On the developing layer base, the coating solution consisting of the following components was coated in an amount of 130 g/m² and then dried to form a developing layer. The components of the coating solution for developing layer are as follows:

| | |
|---|---|
| Water | 46.6 g |
| Antihuman CK-M goat antibody solution (which can inhibit more than 50% of 2000 U/L CKMM when the solution is diluted 1500 times by volume) | 20 g |
| Aqueous 10% solution of nonionic surface active agent | 2.9 g |
| Aqueous 15% solution of polyacrylamide (average molecular weight: 37,000) | 33.8 g |
| Aqueous 20% solution of magnesium chloride | 8.7 g |
| Disodium ethylenediaminetetraacetate | 0.5 g |
| Creatine phosphate (CP) | 1.3 g |
| Adenosine-5'-diphosphate (ADP) | 0.3 g |
| $P^1,P^5$-Di(adenosine-5'-)pentaphosphate (AP5A) | 0.25 g |
| Adenosine-5'-monophosphate (AMP) | 1.2 g |
| N-acetyl-L-cysteine | 0.1 g |
| Nicotinamide adenine dinucleotide in an oxidized form (NAD) | 0.6 g |
| Oxaloacetic acid | 0.07 g |
| N-tris(hydroxymethyl)methyl-2-aminoethanesulfonic acid (TES) | 5.1 g |
| 1 N NaOH | 10.0 g |
| Diaphorase | 1,500 U |
| Glucose-6-phosphate dehydrogenase | 14,000 U |
| Hexokinase (HK) | 19,400 U |
| Ascorbate oxidase | 5,000 U. |

Finally, thus prepared multi-layered composition comprising the support, the detecting agent layer and the developing layer containing the above agents was cut into pieces of 12 mm×12 mm to produce the titled analytical element. It was confirmed that most nitrotetrazolium blue having been incorporated into the detecting agent layer migrated into the developing layer in the resulting analytical element.

EXAMPLE 2

Preparation of Analytical Element for CKMB Employing TAPSO as Buffer Compound

The procedures of Example 1 were repeated except for replacing TES with the same molar amount of TAPSO, to prepare the titled analytical element for CKMB

EXAMPLE 3
Preparation of Analytical Element for CKMB Employing MOPSO as Buffer Compound The procedures of Example 1 were repeated except for replacing TES with the same molar amount of MOPSO, to prepare the titled analytical element for CKMB.

EXAMPLE 4
Preparation of Analytical Element for CKMB Employing MES as Buffer Compound The procedures of Example 1 were repeated except for replacing TES with the same molar amount of MES, to prepare the titled analytical element for CKMB.

Comparison Example 1
Preparation of Analytical Element for CKMB Employing Imidazole as Buffer Compound The procedures of Example 1 were repeated except for replacing 5.1 g of TES and 10.0 g of 1 N—NaOH with 1.5 g of imidazole and 10.0 g of 1 N—HCl, respectively, to prepare the titled analytical element for CKMB.

Comparison Example 2
Preparation of Analytical Element for CKMB Employing Bis-Tris as Buffer Compound The procedures of Example 1 were repeated except for replacing TES with the same molar amount of Bis-Tris, to prepare the titled analytical element for CKMB.

Evaluation of the Analytical Element for CKMB: Formation of ATP During Storage

Each of the analytical elements produced in Examples 1 to 4 and Comparison Examples 1 and 2 was stored for 1 day under the conditions of 45° C. and 11% RH. After the storage was complete, ATP formed in the detecting agent layer and the developing layer was extracted with water. The extracted solution was then injected into a high performance liquid chromatograph (HPLC) to measure the content of ATP. The results are set forth in the following Table 1.

TABLE 1

| Element | Buffer compound | ATP (nano mol) |
|---------|-----------------|----------------|
| Example 1 | TES | 0.00 |
| Example 2 | TAPSO | 0.00 |
| Example 3 | MOPSO | 1.12 |
| Example 4 | MES | 3.02 |
| Com. Example 1 | Imidazole | 27.15 |
| Com. Example 2 | Bis-Tris | 11.52 |

The results shown in Table 1 indicate that the buffer compound having a sulfonic acid group employed in the invention effectively inhibits the formation of ATP in the absence of creatine kinase (or creatine kinase MB isozyme).

Evaluation of Analytical Element for CKMB: Deterioration of Sensitivity During Storage With respect to each of the analytical elements produced in Example 1 and Comparison Example 1, deterioration of the sensitivity was evaluated. The analytical element was stored for 10 days under the conditions of 35° C. and 11% RH, and independently another fresh analytical element was prepared. Onto each of the stored analytical element and the fresh one, two analyte samples (10 U/L and 100 U/L) were spotted. Subsequently, the analytical elements were incubated at 37° C. The spectroscopical measurement at the wavelength of 540 nm was carried out twice (2 minutes and 5 minutes after the incubation began) to quantitatively analyze CKMB according to the reaction rate method. In the measurement, the reaction rate was determined with referring to the calibration curve beforehand obtained. The results are set forth in Table 2.

TABLE 2

| Analytical element | Sample (content of CKMB) | CKMB analysis | |
|---|---|---|---|
| | | fresh element | stored element |
| Example 1 | 10 U/L | 8 U/L | 7 U/L |
| | 100 U/L | 108 U/L | 104 U/L |
| Com. Ex. 1 | 10 U/L | 8 U/L | 22 U/L |
| | 100 U/L | 100 U/L | 113 U/L |

The results set forth in Table 2 indicate the following facts.

The analytical elements employing the buffer compound having a sulfonic acid group according to the invention (Example 1) hardly deteriorates in their sensitivity even after the storage under the severer conditions than usual. On the other hand, the analytical element employing the conventional imidazole buffer (Comparison Example 1) notably deteriorates in sensitivity after the storage although the fresh analytical element has satisfying sensitivity.

What is claimed is:

1. A dry analytical element for quantitatively analyzing creatine kinase comprising:
   a support; and
   a creatine kinase-detecting agent layer provided thereon, in which said creatine kinase-detecting agent layer contains creatine phosphate and adenosine diphosphate for reacting with each other in the presence of creatine kinase to give adenosine triphosphate, a buffer compound having a sulfonic acid group which keeps the creatine kinase-detecting agent layer in the range of pH 5.5 to pH 8.5 for the formation of adenosine triphosphate, and an indicator composition which reacts with adenosine triphosphate to give a spectroscopically detectable compound.

2. The dry analytical element of claim 1, wherein the indicator composition comprises glucose, hexokinase, nicotinamide-adenine dinucleotide or its phosphate in an oxidized form, and glucose-6-phosphate dehydrogenase.

3. The dry analytical element of claim 1, wherein the indicator composition comprises glucose, hexokinase, nicotinamide-adenine dinucleotide or its phosphate in an oxidized form, glucose-6-phosphate dehydrogenase, and a tetrazolium salt.

4. The dry analytical element of claim 1, wherein the indicator composition comprises glycerol, glycerol kinase, L-α-glycerophosphate oxidase, and a leuco dye.

5. The dry analytical element of claim 1, wherein the buffer compound is a Good's buffer.

6. The dry analytical element of claim 5, wherein the Good's buffer is selected from the group consisting of TES, TAPSO, MOPSO and MES.

7. A dry analytical element for quantitatively analyzing creatine kinase MB isozyme comprising:
   a support; and
   a creatine kinase MB isozyme-detecting agent layer provided thereon, in which said creatine kinase MB isozyme-detecting agent layer contains an antibody which specifically inhibits activity of M sub-unit of creatine kinase, creatine phosphate and adenosine diphosphate for reacting with each other in the presence of creatine kinase MB isozyme to give adenosine triphosphate, a buffer compound having a sulfonic acid group which keeps the creatine kinase MB isozyme-detecting agent layer in the range of pH 5.5 to pH 8.5 for the formation of adenosine triphosphate, and an indicator composition which reacts with adenosine triphosphate to give a spectroscopically detectable compound.

8. The dry analytical element of claim 7, wherein the indicator composition comprises glucose, hexokinase, nicotinamide-adenine dinucleotide or its phosphate in an oxidized form, and glucose-6-phosphate dehydrogenase.

9. The dry analytical element of claim 7, wherein the indicator composition comprises hexokinase, nicotin-amide-adenine dinucleotide(phosphate) in an oxidized form, glucose-6-phosphate dehydrogenase and a tetrazolium salt.

10. The dry analytical element of claim 7, wherein the indicator composition comprises glycerol, glycerol kinase, L-α-glycerophosphate oxidase and a leuco dye.

11. The dry analytical element of claim 7, wherein the buffer compound is a Good's buffer.

12. The dry analytical element of claim 11, wherein the Good's buffer is selected from the group consisting of TES, TAPSO, MOPSO and MES.

* * * * *